(12) United States Patent
Hateley et al.

(10) Patent No.: US 7,439,390 B2
(45) Date of Patent: Oct. 21, 2008

(54) PROCESS FOR PREPARING AMINO ACIDS USING THE AMIDOCARBONYLATION REACTION

(75) Inventors: Martin Hateley, Aschaffenburg (DE);
Thomas Häussner, Bad Orb (DE);
Christoph Weckbecker, Gründau (DE);
Klaus Huthmacher, Gelnhausen (DE);
Dieter Buss, Aschaffenburg (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 11/569,319

(22) PCT Filed: May 14, 2005

(86) PCT No.: PCT/EP2005/005296

§ 371 (c)(1),
(2), (4) Date: Nov. 17, 2006

(87) PCT Pub. No.: WO2005/121068

PCT Pub. Date: Dec. 22, 2005

(65) Prior Publication Data

US 2008/0009649 A1    Jan. 10, 2008

(30) Foreign Application Priority Data

Jun. 11, 2004  (GB) ................. 0413090.2

(51) Int. Cl.
*C07C 321/00* (2006.01)
*C07C 51/00* (2006.01)
*B01J 20/34* (2006.01)

(52) U.S. Cl. ................ 562/557; 562/406; 502/24
(58) Field of Classification Search ............... None
See application file for complete search history.

(56) References Cited

U.S. PATENT DOCUMENTS 3,236,597 A * 2/1966 Knap ................. 423/417
3,725,534 A * 4/1973 Reisch ................. 423/417
3,766,266 A   10/1973 Wakamatsu et al.
3,816,337 A * 6/1974 Usami et al. ............. 502/30
3,855,396 A * 12/1974 Kniese et al. ............. 423/417
4,334,042 A * 6/1982 Matsumoto et al. ......... 525/339
4,677,224 A * 6/1987 Commeyras et al. ....... 562/557
4,699,999 A   10/1987 El-Chahawi et al. ....... 562/450
5,097,065 A * 3/1992 Lin ..................... 562/450
5,650,537 A * 7/1997 Beller et al. ............. 562/519
5,756,413 A * 5/1998 Bogdanovic et al. ........ 502/24
5,858,993 A * 1/1999 Pickart ................. 514/60
5,972,999 A * 10/1999 Murad ................. 514/474
6,130,351 A * 10/2000 Stern et al. ............. 562/17
6,162,753 A   12/2000 Geissler et al.
6,979,468 B1 * 12/2005 Pollard ................. 424/643
2002/0026076 A1   2/2002 Huthmacher et al.
2007/0184017 A1 * 8/2007 Faryniarz et al. ......... 424/78.37
2007/0203354 A1 * 8/2007 Ramirez et al. ........... 556/114
2007/0244339 A1 * 10/2007 Hateley et al. ........... 562/406

FOREIGN PATENT DOCUMENTS

| DE | 2 115 985 | 10/1971 |
|---|---|---|
| DE | 4415312 | 11/1995 |
| DE | 195 45 641 A1 | 6/1997 |
| DE | 196 29 717 C1 | 2/1998 |
| EP | 0 338 330 A1 | 10/1989 |
| EP | 0 779 102 A1 | 6/1997 |
| EP | 0 919 539 A1 | 6/1999 |
| EP | 1 048 656 A2 | 11/2000 |
| EP | 0 946 298 B1 | 7/2003 |
| FR | 2 591 221 | 6/1987 |
| JP | 62158239 A * | 7/1987 |
| WO | WO 02/14260 A1 | 2/2002 |

* cited by examiner

*Primary Examiner*—Yvonne Eyler
*Assistant Examiner*—Louisa Lao
(74) *Attorney, Agent, or Firm*—Smith, Gambrell & Russell, LLP

(57) ABSTRACT

The present invention relates to a sequence for the preparation of amino acids, for example alpha-amino acids, in particular methionine, by making use of an amidocarbonylation reaction in the presence of a cobalt carbonyl catalyst and separating the catalyst in the form of a $Co(N\text{-amino acid})_2$ compound.

10 Claims, 1 Drawing Sheet

PROCESS FOR PREPARING AMINO ACIDS USING THE AMIDOCARBONYLATION REACTION

REFERENCE TO RELATED APPLICATIONS

This application claims the benefit of United Kingdom priority Application No. 0413090.2 filed Jun. 11, 2004, and International Application No. PCT/EP2005/005296 filed May 14, 2005, which are relied on and incorporated herein by reference.

INTRODUCTION AND BACKGROUND

The present invention relates to a sequence for the preparation of amino acids, for example alpha-amino acids, in particular methionine, by making use of an amidocarbonylation reaction. During the process, an N-acyl amino acid is synthesised in an amidocarbonylation reaction by making use of a catalyst, and this N-acyl amino acid is then subsequently hydrolysed to the desired amino acid while the carboxylic acid thereby formed is reconverted to the corresponding carboxylic acid amide by reaction with ammonia, followed by dehydration. This carboxylic acid amide can then be re-introduced as a starting material in the initial amidocarbonylation reaction step. According to the invention, the catalyst used during the first reaction step can be recovered and recycled into the first reactor vessel. The synthesis can be conducted in a batch, semi-batch or preferably in a continuous manner.

Amino acids are important products and are correspondingly used in a variety of applications, such as human medicine, the pharmaceuticals industry as well as in the synthesis of a plurality of fine chemicals and active ingredients. In particular they are used as additives in the fodder of many livestock in enantiomerically pure form, but also in the racemic form.

Several methods are employed on an industrial scale to prepare amino acids, such as biotechnological processes, as for example fermentation processes, and hydrolysis of proteins. Chemical syntheses are also used for producing amino acids. One possibility is the Strecker reaction or its variants, such as the Bucherer-Bergs reaction. Still further, the amidocarbonylation reaction is also known to be used for preparing amino acids.

The amidocarbonylation reaction was discovered by Wakamatsu, et al. in 1971 and is disclosed in the German patent application DE-A-2115985. The reaction is catalysed by various transition metal compounds and is a three component reaction between a carboxylic acid amide, an aldehyde and carbon monoxide, either in a pure form or as a mixture with hydrogen (synthesis gas) (see Scheme 1).

Scheme 1
General Reaction Scheme according to the prior art

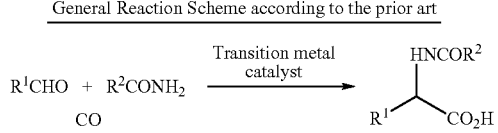

One should bear in mind that the utilisation of the amidocarbonylation reaction is to be regarded as advantageous in comparison to the conventional Strecker synthesis of amino acids or its variants since the amidocarbonylation requires carbon monoxide instead of hydrogen cyanide as one of its integral raw materials. This is of considerable advantage due to the higher price and in particular due to the high toxicity of hydrogen cyanide.

The products of the amidocarbonylation reaction are N-acyl amino acids, having the general formula:

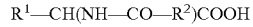

$R^1$ is: hydrogen, a linear, branched or cyclic alkyl group that has from 1 to 10 carbon atoms, especially 1 to 7, or
a linear or branched alkyl group that has from 1 to 10, especially 1 to 6 carbon atoms containing a substituent(s) amido, amino, monoalkylamino, dialkylamino, monoalkylamido, dialkylamido alkoxy, alkylthio, hydroxy, thiol, carboxylic acid or carboxylic acid alkyl ester group(s), or a 1H-imidazole-, phenyl- or 3'-indolyl-, p-hydroxyphenyl or p-alkoxyphenyl residue, whereby the said alkyl or alkoxy group has 1 to 3 carbon atoms,
most preferred for $R^1$ is a linear or branched alkyl group that has from 1 to 10, especially 1 to 6 carbon atoms containing a substituent(s) amido, alkoxy, alkylthio or a phenyl or p-alkoxyphenyl residue, whereby the said alkyl group(s) has 1 to 3 carbon atoms.

$R^2$ is: hydrogen or a linear, branched or cyclic alkyl group having 1 to 10 carbon atoms, or
a linear, branched or cyclic alkyl group having 1 to 10 carbon atoms, containing a substituent(s) amido, monoalkylamido, dialkylamido hydroxy, alkyoxy, thioalkoxy group(s) or
a substituted or non-substituted aryl or benzyl group, where the substituent(s) may be a hydroxy, alkoxy, fluoro, chloro, bromo or a trialkylamino group, whereby the said alkyl group has 1 to 3 carbon atoms.

The said N-acyl amino acids are starting materials especially for the α-amino acids:
asparagine, aspartic acid, cystein, glutamine, glutamic acid, histidine, serine, threonine, tryptophan, tyrosine, most especially for alanine, glycine isoleucine, leucine, methionine, phenylalanine, valine.

Substituted hydantoins can also be prepared instead of N-acyl amino acids. In such a case, ureas are used as starting materials, as for example disclosed in the European patent application EP 1 048 656 A2.

The European patent application EP 338 330 A1 and the German patent application DE 19629717 also disclose the synthesis of various N-acyl amino acids via the amidocarbonylation reaction. DE 4415312 and DE 19545641 deal with that reaction as well, for example in the case of the industrial preparation of sarcosinates.

However, no prior art suggests a process to prepare amino acids, in particular methionine, comprising of the amidocarbonylation reaction with convenient withdrawal of the used catalyst, hydrolysis of the N-acyl amino acid formed, and conversion of the by-product carboxylic acid formed during the hydrolysis into a carboxylic acid amide.

With regard to this, one should note that the aspect of catalyst recycling of the expensive transition metal catalyst used in the amidocarbonylation is also an important target from an economic point of view, that is avoiding the high costs involved in the acquisition of new catalyst and the disposal of spent catalyst. Recycling of the catalyst is furthermore advantageous with respect to environmental reasons due to the often high toxicity of transition metals and compounds related thereto.

A process for the recovery of cobalt carbonyl catalysts is, for example, described in the European patent EP 779 102 B1. According to that prior art, the active catalyst was initially oxidised after the reaction to the more stable cobalt (II) form, which was then extracted into aqueous solution, precipitated as the hydroxide and subsequently converted into a melt consisting of the hydroxide and N-acyl amino derivative which can be used for regeneration of the active catalyst under a synthesis gas atmosphere.

However, the same disadvantage as mentioned above occurs according to that prior art. For example, handling problems occur during the precipitation and drying of cobalt hydroxide. Still further, if the process were to be run in a continuous way, higher expenses would be incurred. Summing up, the processes suggested in the prior art for catalyst recovery during an amidocarbonylation reaction are not suitable for the large scale industrial synthesis of amino acids, especially methionine, due to the variety of handling problems, occurring in particular for such amino acids containing sulphur, as methionine.

There is, however, a strong need to find a way to recycle the catalyst used during the synthesis of amino acids via the amidocarbonylation. The carbonyl catalyst makes it possible to make use of carbon monoxide as a starting material, which is easier to handle and more widely available than hydrogen cyanide.

SUMMARY OF INVENTION

It is the object of the present invention to provide an amidocarbonylation reaction for producing amino acids providing a method of regenerating and recycling the catalyst employed in the amidocarbonylation reaction to increase the efficiency of the amidocarbonylation reaction and to limit harmful emissions and environmental damage.

These objects have been solved by a process as disclosed in the patent claims. The process is also suited for producing sulphur containing amino acids, such as methionine, which might be expected to cause problems with the transition metal catalyst.

Catalyst recycling means preferably regeneration of the catalyst, specifically after removal of the product from the reaction mixture, and reuse of the regenerated catalyst. According to an aspect of the invention, regeneration of the catalyst from the reaction solution takes place by means of a chemical conversion into an intermediate, from which the active catalyst can be later regenerated, if necessary in a further separate step, and reused. According to the invention the catalyst is separated, regenerated and subsequently reused.

In accordance with a preferred embodiment, the preparation of amino acids occurs in a continuous manner. A particularly preferred process is directed to the production of methionine.

The process according to the invention comprises the following steps:

a) Amidocarbonylation of an aldehyde with an carboxylic acid amide to give an N-acyl amino acid in the presence of a Co-catalyst, carbon monoxide and hydrogen, b) feeding an oxygen containing gas into the heated reaction mixture after completion of reaction a) and conversion of the used catalyst to an intermediate Co(N-acyl-amino-acid)$_2$, which precipitates from solution, preferably regeneration of the catalyst from said intermediate by conversion with synthesis gas to give said cobalt carbonyl catalyst;

c) hydrolysis of the N-acyl amino acid resulting from step a) to obtain the subsequent amino acid, and d) in a preferred case, conversion of the carboxylic acid resulting from step c) preferably with ammonia, resulting in the regeneration of the carboxylic acid amide used in step a), while the catalyst used in step a) is withdrawn from the reaction solution and regenerated as shown in step b) and introduced into the reaction medium of step a) for another amidocarbonylation reaction.

BRIEF DESCRIPTION OF DRAWING

The invention will be further understood with reference to the accompanying drawing which shows the equation for the process of the invention.

DETAILED DESCRIPTION OF INVENTION

Figure 1:
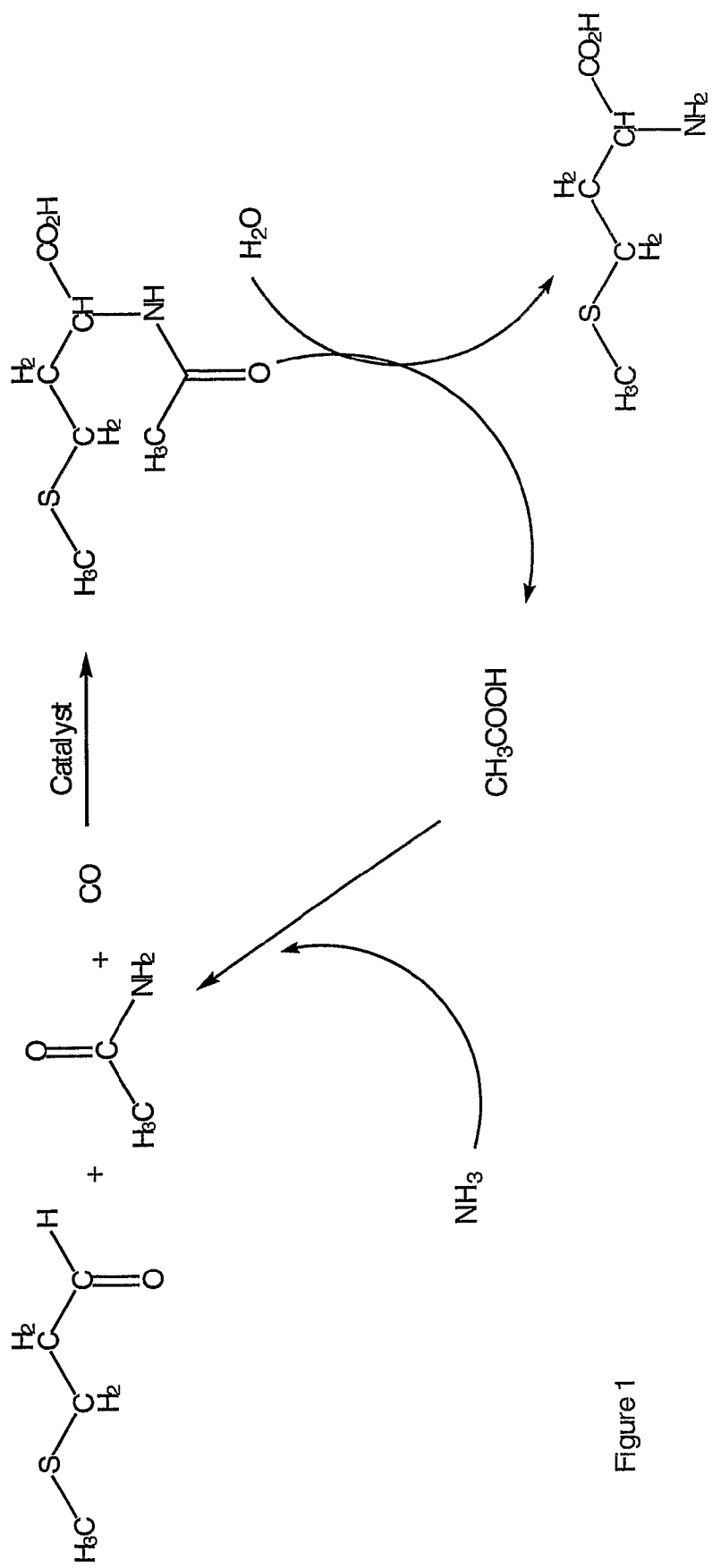

This overall process is illustrated in FIG. 1 for the preferred case of methionine synthesis. As apparent from FIG. 1, the raw materials required are an aldehyde, for the case of methionine synthesis as demonstrated in FIG. 1, 3-(methylthio)propanal, carbon monoxide and ammonia. The ammonia is transported into the reaction in the form of acetamide used in step a) and has the function of a nitrogen carrier. Acetic acid formed during the hydrolysis step is reconverted into acetamide by reaction with ammonia and subsequent dehydration.

The hydrolysis occurring during step c) is known to the skilled person and is, for example, disclosed in the patent application WO 02/14260. Details of the regeneration reaction step of the amide can be taken from EP 919 539 A1.

In the first step, the aldehyde and amide are mixed in a solvent under an inert atmosphere. The molar ratio of the aldehyde to the amide can be in the range of 1:1 to 1:5, preferably in the range of 1:1 to 1:1.5.

A suitable and preferred solvent is dipolar and aprotic. Examples of these are sulphones; dimethyl sulphoxide; esters, like methyl acetate, ethyl acetate or butyl acetate; ketones, like acetone or methylisobutylketone; ethers, like tetrahydrofuran, dioxan, methyl tert-butyl ether, diisopropyl ether; amides, like dimethyl acetamide, DMF and N-methylpyrrolidine, aromatics, like toluene; nitrites, like acetonitrile and carboxylic acids.

The catalyst is preferably preformed in a separate reactor vessel from the desired cobalt precursor with carbon monoxide and hydrogen. Preferred amounts of the catalyst are in the range of 0.1 mol % to 5 mol %, with respect to the reacting aldehyde, particularly preferred in the range of 1 to 2 mol % carbonyl compounds of cobalt are used. The presence of heteroatoms, especially sulphur, in the starting aldehyde does not negatively influence the yield of product, when cobalt is used as the metal in the catalyst.

The solution of the amide and the aldehyde is put into a pressure resistant vessel and the vessel is pressurised with synthesis gas.

The pressure of synthesis gas is set at 20 to 200 bar (20,000 to 200,000 hPa), especially preferred are 80 to 130 bar (80,000 to 130,000 hPa).

Synthesis gas with $H_2/CO$ ratios of 1:1 to 1:9 can be used, whereby the ratio of 1:8 to 1:9 is preferred. The pressure is maintained constant during the reaction.

After pressurization is completed, the vessel is heated to a temperature in the range of 40° C. to 150° C., preferably between 60° C. and 120° C., more preferred between 60° C. and 80° C.

During the entire reaction period the reaction solution is agitated, preferably by means of stirring, enabling a maximal gas absorption into the solution.

According to a preferred embodiment of the process of the present invention, a solution of the starting amide and the catalyst are added to an organic solvent in a pressure vessel.

After pressurisation to the above mentioned pressure and heating to the above mentioned temperature, the aldehyde starting material is fed into the pressure vessel by means of a pump at a constant linear or more preferably non-linear rate during the reaction. In this way the selectivity of the reaction can be increased, and the amount of unwanted side products can be diminished.

After a reaction time of between 20 minutes and 6 hours, or, if the process is run continuously, after an average residency time of the same, the reaction solution is cooled to 10° C. to 40° C., preferably 20° C. to 30° C. The synthesis gas atmosphere is then released and the vessel is subsequently re-pressurised to between 8 and 12 bar (8,000 to 12,000 hPa) with air. The solution is stirred at this pressure. The dispersal of gas into the solution optimises the yield. After approximately 2-3 hours, the volume of the solution is preferably reduced by around 25% in vacuo.

The remaining solution is then heated to preferably between 60° C. and 80° C. whilst having an oxygen containing gas, especially air bubbled through it. Pink Co(N-acyl-amino acid)$_2$ precipitates and is withdrawn by filtration.

Conversion of separated Co(N-acyl-amino acid)$_2$ into the active carbonyl catalyst can then be accomplished using a known procedure by heating a solution or slurry of Co(N-acyl-amino acid)$_2$ in a preferably polar aprotic solvent under a synthesis gas atmosphere (EP-B-0 946 298).

The filtrate obtained after removal of Co(N-acyl-amino acid)$_2$ is then cooled to preferably between 5° C. to 20° C. and after a suitable amount of time the crystalline product, N-acyl amino acid, can be isolated by filtration.

After removal of the last traces of organic solvent by means of drying, the product N-acyl amino acid is transferred to a pressure resistance reaction vessel containing water. The concentration of the N-acyl amino acid in the water is in the range of 0.1 molar to 5 molar. The reaction solution is then heated to a temperature in the range of from 120° C. to 180° C., preferably between 140° C. and 160° C. Further details of such a hydrolysis process are known by the skilled person and are, for example, described in WO 02/14260. After an average residence time of between 4 to 6 hours, the solution is cooled to a temperature in the range of from 10° C. to 40° C. where upon the product amino acid precipitates. After filtration and drying, the desired product amino acid is obtained.

In a preferred embodiment of the invention the filtrate containing the carboxylic acid formed during the hydrolysis, as well as trace amounts of the starting N-acyl amino acids, is mixed with an organic solvent immiscible with water in a counter flow extraction column. Preferred organic solvents are cyclohexanone, butanone, ethyl acetate and MIBK, particularly preferred is MIBK (methyl isobutyl ketone). The carboxylic acid is transferred into the organic layer and the aqueous solution containing impurities and the remaining starting material is returned to the hydrolysis reaction vessel. A part of the said solution is also discarded in the form of a purge, in order to prevent the build-up of unwanted side products. The organic solvent containing the carboxylic acid (in particular acetic acid) is then fed into a second counter flow extraction column, where an aqueous solution of ammonia is used as the counter flow. The reaction leads to the formation of an ammonium carboxylate in the aqueous phase which is subjected to a dehydration reaction to obtain a carboxylic acid amide. Details are known to the skilled person, or for example described in EP 919 539 A1. The organic solvent from the organic layer is separated and after drying recycled in the first extraction column.

The single processes are preferably conducted as connected processes, which is an advantage during large scale production.

The following examples are intended to illustrate the invention, without having a limiting effect.

EXAMPLES

Example 1

3.02 g acetamide, 5.36 g 3-(methylthio)propanal (97% purity) and 0.342 g of $CO_2(CO)_8$, the cobalt catalyst precursor were dissolved in 50 ml butyl acetate in a 100 ml laboratory autoclave. The reactor was pressurised to 130 bar (130,000 hPa) with 1:1 $H_2$/CO synthesis gas and heated to 70° C. whilst stirring. The reaction was stirred for 8 hours after which the reactor vessel was cooled to room temperature and the pressure released. Analysis of the reaction mixture using HPLC gave:

| | |
|---|---|
| MMP conversion | 100% |
| Yield (N-acetyl methionine) | 92.2% |
| Selectivity (N-acetyl methionine) | 92.2% |
| Side products included approximately 1,3-bis(methylthio)propane. | 5% |

The product N-acetyl methionine was recovered by filtration of the product solution. Washing the solid with chilled ethyl acetate and drying in vacuum gave N-acetyl methionine as a white solid.

Example 2

3.02 g of acetamide and 0.142 g of $CO_2(CO)_8$, the cobalt catalyst precursor, were dissolved in 20 ml of ethyl acetate in a 100 ml laboratory autoclave. The reactor was pressurised to 130 bar (130,000 hPa) with 1:1 $H_2$/CO synthesis gas and heated to 80° C. whilst stirring. After 5 minutes a solution of 5.36 g MMP (97%) in 25 ml of ethyl acetate was slowly added using an HPLC pump at a rate of 0.42 ml/min up to 50% addition, 0.21 ml/min up to 75% addition, 0.13 ml/min up to 91% addition and 0.08 ml/min up to 100% addition. Subsequently, 5 ml of ethyl acetate were added to the reaction in order to rinse the pump and addition line. The reaction was continued for a further 2.5 hours, after which the reactor vessel was cooled to room temperature and the pressure released. Analysis of the reaction mixture using HPLC gave:

| | |
|---|---|
| MMP conversion | 96% |
| Yield (N-acetyl methionine) | 89.9% |
| Selectivity (N-acetyl methionine) | 93.6% |

Side products included <1% N-acetyl methionine ethyl ester and approximately 4% 1,3-bis(methylthio)propane.

Example 3

N-Acetyl methionine formed according to Example 1 was hydrolysed to methionine and the acetic acid formed reacted with ammonia to form acetamide.

6.40 g of N-acetyl methionine were dissolved in 50.4 g of water. The solution was transferred to a 100 ml pressure vessel and heated to 165° C. whilst stirring for 5 hours, during which the pressure remained constant at about 9 bar (9,000 hPa).

After cooling to room temperature, the solution was filtered and the recovered methionine was dried in vacuum.

| N-Acetyl methionine conversion | 93% |
| --- | --- |
| Yield (methionine) | 90% (60% isolated) |
| Yield (acetic acid) | 92% |

The presence of the dipeptide Met-Met as well as the diketopiperazine formed from two methionine molecules were detected in HPLC (>0.5% overall).

The filtrate containing the acetic acid formed during the hydrolysis, as well as trace amounts of the starting N-acyl amino acids, is mixed with MIBK in a counter flow extraction column.

The acetic acid is transferred into the organic layer and the aqueous solution containing impurities and the remaining starting material is returned to the hydrolysis reaction vessel. A part of the said solution is also discarded in the form of a purge, in order to prevent the build-up of unwanted side products. The organic layer containing the acetic acid is then fed into a second counter flow extraction column, where an aqueous solution of ammonia is used as the counter flow. The reaction leads to the formation of an ammonium carboxylate which is subjected to a dehydration reaction for obtaining acetamide as described in EP 919 539 A1. The MIBK is then removed and after drying recycled in the first extractor column.

Example 4

Production of methionine and removal of the used catalyst by forming Co(N-Acyl amino acid)$_2$ 261 g of MMP (99% pure), 151 g of acetamide and 17.1 g of CO$_2$(CO)$_8$ were dissolved in 2.5 l of ethyl acetate in a 5 l pressure vessel. The reactor vessel was then heated to 80° C. and pressurised to 130 bar of synthesis gas (ratio of CO/H$_2$ 1:1) and the reaction mixture was stirred for 5 hours. After cooling to room temperature, the synthesis gas pressure in the reactor was released and the reactor re-pressurised with 10 bar (10,000 hPa) of air and stirred for several hours. After removal of the reaction solution from the pressure vessel and subsequent concentration of the reaction solution to approximately 75%, the remaining solution was heated to 80° C. and air was bubbled through this solution at a rate of 21 ml/s until the solution did not change optically any more. The hot solution was filtered and the pink precipitate of Co(N-Ac-Met)$_2$ washed with warm ethyl acetate. The filtrate portions are combined and cooled to 5° C., whereupon the product N-acetyl methionine crystallises out and can be isolated by filtration and hydrolysed to obtain methionine.

| Yield of Co(N-Ac-Met)$_2$ | 90% |
| --- | --- |
| Total yield of N-acetyl methionine | 80.7% |

What is claimed is:

1. A process for producing an amino acid comprising the following reaction steps:
   a) reacting an aldehyde with an amide and carbon monoxide and hydrogen as a heated reaction mixture in an amidocarbonylation reaction to give an N-acyl amino acid in the presence of a cobalt carbonyl catalyst,
   b) precipitating Co(N-acyl-amino acid)$_2$ by feeding an oxygen containing gas into the heated reaction mixture after completion of reaction a), and separating precipitated Co(N-acyl-amino acid)$_2$, and
   c) hydrolyzing the remaining dissolved N-acyl amino acid to obtain the subsequent amino acid.

2. The process according to claim 1, wherein said N-acyl amino acid has the formula $$R^1\text{---CH(NH---CO---}R^2)\text{COOH} \quad (I)$$

wherein
R$^1$ is: hydrogen, a linear, branched or cyclic alkyl group that has from 1 to 10 carbon atoms, or a linear or branched alkyl group that has from 1 to 10, carbon atoms containing as a substituent amido, amino, monoalkylamino, dialkylamino, monoalkylamido, dialkylamido alkoxy, alkylthio, hydroxy, thiol, carboxylic acid or carboxylic acid alkyl ester group(s), or a 1H-imidazole-, phenyl- or 3'-indolyl-, p-hydroxyphenyl or p-alkoxyphenyl residue, whereby the said alkyl or alkoxy group has 1 to 3 carbon atoms,
R$^2$ is: hydrogen or a linear, branched or cyclic alkyl group having 1 to 10 carbon atoms, or a linear, branched or cyclic alkyl group having 1 to 10 carbon atoms, containing as a substituent(s) amido, monoalkylamido, dialkylamido hydroxy, alkyoxy, thioalkoxy group or a substituted or non-substituted aryl or benzyl group, where the substituent may be a hydroxy, alkoxy, fluoro, chloro, bromo or a trialkylamino group, the said alkyl group having 1 to 3 carbon atoms.

3. The process according to claim 1, further comprising the reaction step to regenerate the catalyst, whereby said Co(N-acyl amino acid)$_2$ is
   a) slurried or dissolved in an appropriate solvent,
   b) heated under a synthesis gas atmosphere, and
   c) regenerated Co-carbonyl catalyst is fed to the amidocarbonylation reaction.

4. The process according to claim 1, further comprising a reaction step to regenerate the amide used in step a), whereby
   a) after separation of the amino acid carboxylic acid formed by hydrolysis is extracted and brought into contact with aqueous ammonia,
   b) formed ammonium carboxylate is separated,
   c) said carboxylate is subjected to a dehydration reaction for obtaining carboxylic acid amide, and
   d) said amide is fed to the amidocarbonylation process.

5. The process according to claim 1, wherein 3-(methylthio)propanal is the aldehyde and the subsequent amino acid is methionine.

6. The process according to claim 1, wherein the process is conducted in a continuous manner.

7. The process according to claim 2, wherein R$^1$ is a linear, branched or cyclic alkyl of 1 to 7 carbons or a linear or branched alkyl of 1 to 6 carbons.

8. The process according to claim 2, further comprising a reaction step to regenerate the catalyst, whereby said Co(N-acyl amino acid)$_2$ is
   a) slurried or dissolved in an appropriate solvent,
   b) heated under a synthesis gas atmosphere, and
   c) regenerated Co-carbonyl catalyst is fed to the amidocarbonylation reaction.

9. The process according to claim 2, further comprising a reaction step to regenerate the amide used in step a), whereby
   a) after separation of the amino acid carboxylic acid formed by hydrolysis is extracted and brought into contact with aqueous ammonia,
   b) formed ammonium carboxylate is separated,
   c) said carboxylate is subjected to a dehydration reaction for obtaining carboxylic acid amide, and d) said amide is fed to the amidocarbonylation process.

10. The process according to claim 3, further comprising a reaction step to regenerate the amide used in step a), whereby
  a) after separation of the amino acid carboxylic acid formed by hydrolysis is extracted and brought into contact with aqueous ammonia,
  b) formed ammonium carboxylate is separated,
  c) said carboxylate is subjected to a dehydration reaction for obtaining carboxylic acid amide, and
  d) said amide is fed to the amidocarbonylation process.

* * * * *